(12) United States Patent
Noack

(10) Patent No.: US 7,507,219 B2
(45) Date of Patent: Mar. 24, 2009

(54) METHOD FOR DETERMINING THE INTRAPERITONEAL VOLUME AND DEVICE FOR PERITONEAL DIALYSIS

(75) Inventor: Joachim Noack, Bad Neustadt (DE)

(73) Assignee: Fresenius Medical Care Deutschland GmbH (DE)

( * ) Notice: Subject to any disclaimer, the term of this patent is extended or adjusted under 35 U.S.C. 154(b) by 1449 days.

(21) Appl. No.: 09/973,968

(22) Filed: Oct. 9, 2001

(65) Prior Publication Data
US 2002/0107474 A1  Aug. 8, 2002

(30) Foreign Application Priority Data
Oct. 10, 2000  (DE) ............................... 100 49 900

(51) Int. Cl.
*A61M 1/00* (2006.01)
*B01D 11/00* (2006.01)
*B01D 61/00* (2006.01)

(52) U.S. Cl. ...................... 604/28; 604/29; 210/645

(58) Field of Classification Search .............. 604/29, 604/28, 502–505, 5.01–5.04; 210/645–647
See application file for complete search history.

(56) References Cited

U.S. PATENT DOCUMENTS

| | | | | |
|---|---|---|---|---|
| 3,620,215 A | * | 11/1971 | Tysk et al. ................... 604/29 |
| 4,668,400 A | * | 5/1987 | Veech ....................... 210/647 |
| 4,976,683 A | * | 12/1990 | Gauthier et al. ............... 604/29 |
| 5,542,919 A | * | 8/1996 | Simon et al. .................. 604/29 |
| 5,643,201 A | * | 7/1997 | Peabody et al. ............... 604/31 |
| 5,670,057 A | | 9/1997 | Chen et al. |
| 6,049,727 A | * | 4/2000 | Crothall ..................... 600/310 |
| 6,409,699 B1 | * | 6/2002 | Ash ........................... 604/29 |

FOREIGN PATENT DOCUMENTS

DE 19901078 C1 * 2/2000
EP 0149001 * 9/1984

* cited by examiner

*Primary Examiner*—Matthew F Desanto
(74) *Attorney, Agent, or Firm*—Kenyon & Kenyon LLP

(57) ABSTRACT

A method and device are provided for determining a intraperitoneal volume during peritoneal dialysis. The method and device can be used in conjunction with a dialysis machine wherein a first circuit peritoneal solution from a patient's peritoneal cavity is carried past one side of a semipermeable membrane and dialyzing fluid in a second circuit is carried past the other side of the membrane. The concentration of an endogenous substance (which during peritoneal dialysis passes through the peritoneum into the peritoneal cavity) is measured during the treatment. The intraperitoneal volume is calculated from the measured variation in concentration of the endogenous substance in the peritoneal solution. Preferably, the endogenous substance is albumin. The concentration of the endogenous substance preferably is measured at two successive times. After the first measurement, a predetermined volume of fluid $\Delta V$ is withdrawn from or added to the first circuit.

5 Claims, 3 Drawing Sheets

METHOD FOR DETERMINING THE INTRAPERITONEAL VOLUME AND DEVICE FOR PERITONEAL DIALYSIS

FIELD OF THE INVENTION

The invention relates to a method for determining the intraperitoneal volume during peritoneal dialysis and a device for peritoneal dialysis having a means for determining the intraperitoneal volume.

BACKGROUND OF THE INVENTION

In continuous ambulatory peritoneal dialysis ("CAPD"), dialysate is instilled into the peritoneal cavity, i.e., the patient's abdominal cavity, via a permanently implanted peritoneal catheter. The dialysate remains in the abdominal cavity for several hours. At the end of this cycle, the dialysate is drained. The exchange of fluid and dissolved substances between the blood in the peritoneal capillaries and the dialysate may result in adequate elimination of substances usually eliminated with the urine.

Known devices for so-called continuous flow peritoneal dialysis ("CFPD") have a dialyzer that is divided into first and second compartments by a membrane. The first compartment is in communication with the peritoneal catheter via a first sterile circuit, while the second compartment is in communication with a device for delivering dialyzing fluid via a second circuit. The circuits are separated from one another by the membrane of the dialyzer. During CFPD, peritoneal solution from the peritoneal cavity is carried past one side of the membrane, while dialyzing fluid is carried past the other side of the membrane. Exchange of materials between the peritoneal solution and the continuously delivered fresh dialyzing fluid takes place at the membrane. At the same time, toxins on the membrane are removed from the peritoneal solution and, vice-versa, substances resorbed by the patient, such as glucose, are restored.

Owing to the exchange of materials, the concentration gradient of the toxins and the osmotic gradient of the solution in the peritoneal cavity, are maintained relative to the environment, so that a steady secretion of fluid over the peritoneum takes place in the peritoneal cavity. This may result in a practically unlimited increase in fluid in the peritoneal cavity. The aforementioned increase in fluid is also called patient's ultrafiltration.

Therefore, determination of the intraperitoneal volume, i.e., the volume of fluid in the peritoneal cavity, is essential for protection of the patient against "overfilling." If the intraperitoneal volume is known, the excess fluid can be removed from the first circuit through the membrane of the dialyzer. The known CFPD devices have an ultrafiltration means for this purpose.

The intraperitoneal volume may be determined empirically or by a drain in the patient. EP A 0,149,001 describes a peritoneal dialysis device in which the ultrafiltration rate is controlled as a function of the intraperitoneal volume, so that "overfilling" of the patient is precluded. Ultrafiltration control is based on measurement of dilution. The peritoneal dialysis device comprises a closed circuit, in which dialyzing fluid circulates and to which a substance is added from outside whose secretion and resorption rate is negligible during the entire duration of treatment. The concentration of this substance in the peritoneal solution continuously decreases with increasing volume. During treatment the concentration is measured and compared with the initial concentration at the start of treatment. When a difference between the measured concentration and the initial concentration is detected, the ultrafiltration means withdraws fluid from the peritoneal cavity until the initial concentration in the dialyzing fluid has been reestablished.

A drawback with the device disclosed in EP A 0,149,001 is that an exogenous substance must be added to the dialyzing fluid. Hence, incompatibilities cannot be ruled out. Further secretion or resorption of the substance may result in defective control of the ultrafiltration rate.

SUMMARY OF THE INVENTION

The object of the invention is to indicate a method that allows simple determination of the intraperitoneal volume without the risk of incompatibilities. An additional object of the invention is to procure a peritoneal dialysis device that permits simple determination of the intraperitoneal volume without risk to the patient.

Determination of the intraperitoneal volume is based on measurement of the concentration of an endogenous substance that passes through the peritoneum into the peritoneal cavity during peritoneal dialysis. This is desirable in that exogenous substances need not be added. Therefore, determination of the intraperitoneal volume is less cumbersome and less costly. In addition, incompatibilities can be ruled out.

During peritoneal dialysis, peritoneal solution in a first circuit flows along one side of a membrane, while dialyzing fluid in a second circuit flows along the other side of the membrane. A circuit is not necessarily a closed system, but can also be a system in which fluid flows in from a source and is discharged into a drain. Each of the circuits may again comprise several partial circuits.

The membrane between the first and the second circuit preferably is not permeable to the endogenous substance. Should the membrane nevertheless be permeable, the reduction in concentration of the substance owing to passage of the same through the membrane should be appropriately corrected upon evaluation of the measurement results.

A suitable endogenous substance for the measurement of concentration preferably is albumin. Because of its high molecular weight of over 60 K Dalton, albumin is transported very slowly through the peritoneum, so that the concentration of albumin varies very slowly due to secretion or resorption processes in the patient. In addition, filter membranes customary in hemodialysis are not permeable to this substance.

In principle, measurement of the concentration of the endogenous substance in the peritoneal solution may take place over the entire duration of treatment. However, it requires that secretion or resorption of the substance be disregarded. Advantageously, for determination of the concentration, two measurements are made at two immediately successive times, while a predetermined volume of peritoneal solution is withdrawn from the first circuit between the measurements. Instead of a withdrawal of fluid, a controlled addition of fluid into the patient's circuit may alternatively be made, so that not only the concentration but also the dilution of albumin as an endogenous substance can be measured. The intraperitoneal volume is then calculated from the concentrations measured at two successive times and the volume withdrawn. This is desirable in that secretion or resorption of the endogenous substance in this period of time may be disregarded. Therefore, the measurement of dilution may in principle alternatively be made with an exogenous substance whose secretion or resorption over the entire duration of treatment is not be disregarded.

The patient's ultrafiltration rate advantageously is determined from the variation in intraperitoneal volume. At this ultrafiltration rate, fluid is then withdrawn from the first circuit in order to avoid "overfilling" of the patient. In order to be able to continuously correct the ultrafiltration rate, a plurality of these measurements preferably is made over the entire duration of treatment.

The means for determining the peritoneal volume includes a measuring unit for determination of the concentration of the endogenous substance as well as a calculating and evaluation unit that determines the intraperitoneal volume from a variation in concentration of the endogenous substance. Absorption or transmission detectors, for example, may be used as sensors.

DETAILED DESCRIPTION OF THE DRAWINGS

Figure 1:
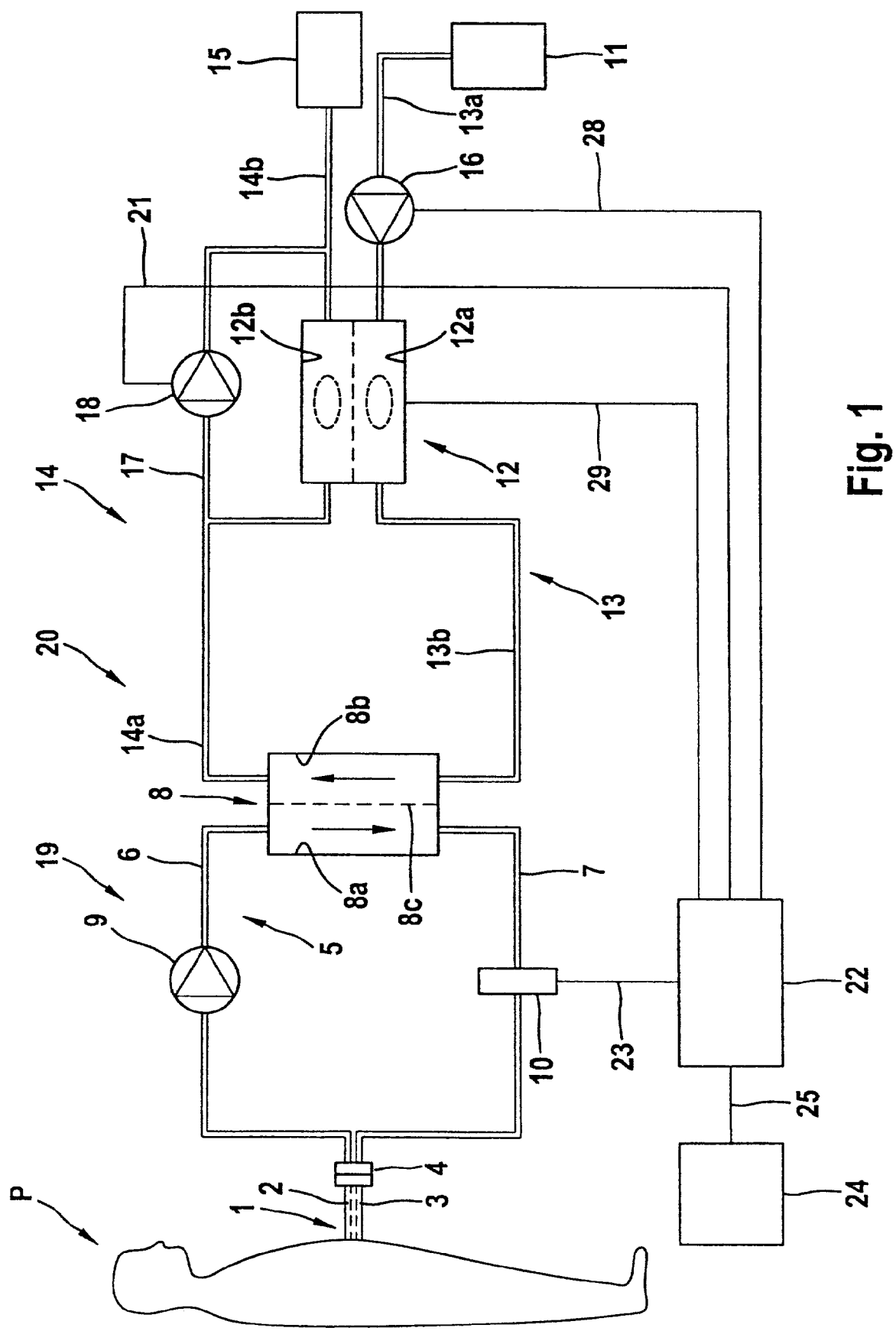
FIG. 1 illustrates, in simplified representation, a first example of a peritoneal dialysis device having a means for determining the peritoneal volume.

FIG. 1 shows the essential components of the device for peritoneal dialysis in a simplified schematic representation. The peritoneal dialysis device comprises a permanently implantable peritoneal catheter 1, which has first and second lumens 2 and 3 for, respectively, delivery of a peritoneal solution into the peritoneal cavity and drainage of the solution from the patient's peritoneal cavity. The peritoneal catheter 1 is connected by a connector 4 with a hose transfer system 5, which has a feed line 6 and a drain line 7. One end of the feed line 6 is connected with the first lumen 2 of the peritoneal catheter, while the other end of the feed line is connected with the inlet of a first compartment 8a of a dialyzer 8 divided by a semipermeable membrane 8c into the first compartment 8a and a second compartment 8b. The membrane has a first side 8d facing the first compartment 8a and a second side 8e facing the second compartment 8b. The outlet of the first compartment 8a of the dialyzer 8 is connected to one end of the drain line 7, while the other end of the drain line is connected with the second lumen 3 of the peritoneal catheter 1.

An occluding hose pump 9 is provided in the feed line 6 for pumping the peritoneal solution from the peritoneal cavity of the patient P. A measuring unit 10 measures an endogenous substance in the peritoneal solution which crosses the peritoneum into the peritoneal cavity during peritoneal dialysis, but to which the membrane 8c of the dialyzer is not permeable. The peritoneal solution is delivered by the pump 9, via the feed line 6, from the peritoneal cavity to the first compartment 8a of the dialyzer 8 and returned to the peritoneal cavity again via the drain line 7 and the measuring unit 10. While peritoneal solution in a first circuit 19 flows along the first side 8d of the membrane 8c of the dialyzer 8, fresh dialyzing fluid in the second circuit 20 flows along the second side 8e of the membrane.

Fresh dialyzing fluid is provided in a dialyzing fluid source 11. A balancer 12, represented only schematically, which advantageously contains two balance compartments 12a, 12b that in each instance are divided by a membrane into two balance compartment halves, is provided for balancing fresh and spent dialyzing fluid. Such a balancer is disclosed, for example, in DE A 28 38 414, which is fully incorporated herein by reference.

A first section 13a of a feed line 13 connects the dialyzing fluid source 11 with the balancer 12, while the second section 13b of the feed line connects the balancer 12 with the second compartment 8b of the dialyzer 8. The first section 14a of a drain line 14 connects the second compartment 8b of the dialyzer 8 with the balancer 12, while the second section 14b of the drain line 14 connects the balancer 12 with a drain 15. An ultrafiltration line 17, which leads to the second section 14b of the feed line, branches off from the first section 14a of the feed line. An ultrafiltration pump 18, by which fluid can be withdrawn from the first circuit 19 across the membrane 8c of the dialyzer 8, is provided in the ultrafiltration line 17. A pump 16 in the first section 13a of the feed line 13 delivers fresh dialyzing fluid to the balancer 12.

The pump 16 is connected via a control line 28 and the ultrafiltration pump 18 is connected via a control line 21 with a control unit 22, which in turn is connected via a data line 23 with the measuring unit 10. A calculating and evaluation unit 24 is connected with the control unit via a data line 25. The control unit 22 is also connected with the balancer 12 via a control line 29, so that the balancer 12 can be controlled in such a way that a defined quantity of fluid is delivered to the first circuit 5 via the dialyzer 8.

The control unit 22, the calculating and evaluation unit 24, and the measuring unit 10, are components of a device for determining the intraperitoneal volume. The calculating and evaluation unit 24 and the control unit 22 may be a microcomputer, which generally is present in the known dialysis devices.

The manner in which the device determines the intraperitoneal volume is now described. The concentration of albumin in the patient's blood is about 40 g/L. Convective and diffusive transport of albumin, as an endogenous substance, into the peritoneal solution takes place during dialysis, so that the albumin concentration of the peritoneal solution continuously increases. Because of the great molecular size of albumin of about 60 K Dalton, the transport of albumin from the blood into the peritoneal solution is very slow and is strongly determined by convective transport. The course of the albumin concentration over time during peritoneal dialysis at constant glucose concentration of the peritoneal solution is shown by the dashed curve in FIG. 2a.

Figure 2A:
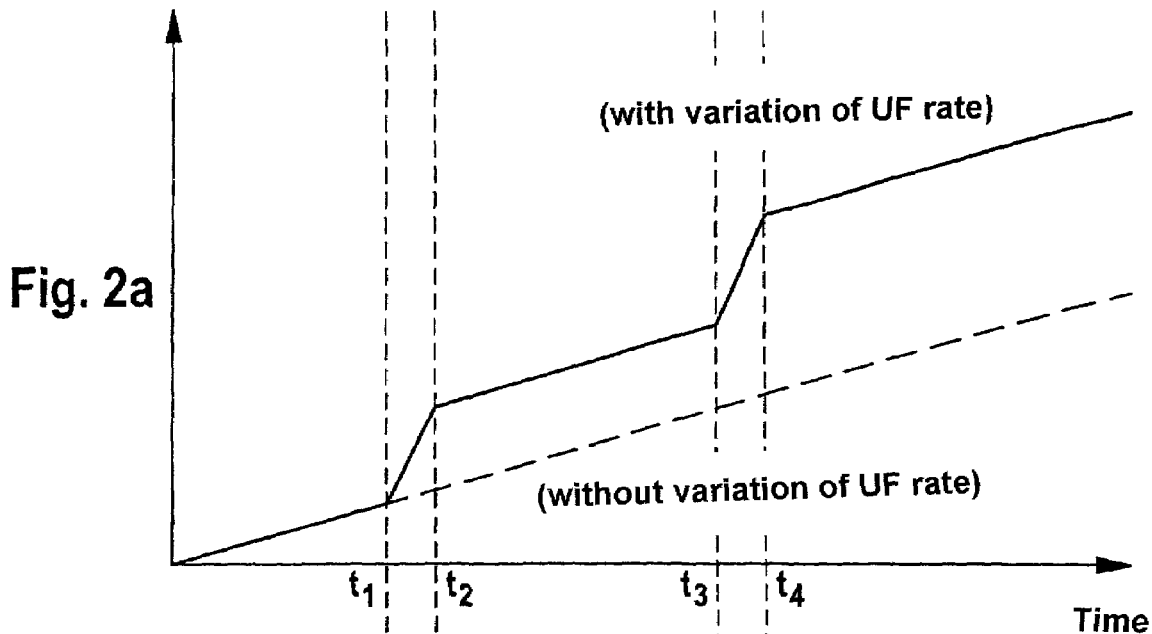
FIG. 2a is a graph of the concentration of albumin vs. time during dialysis treatment.
Figure 2B:
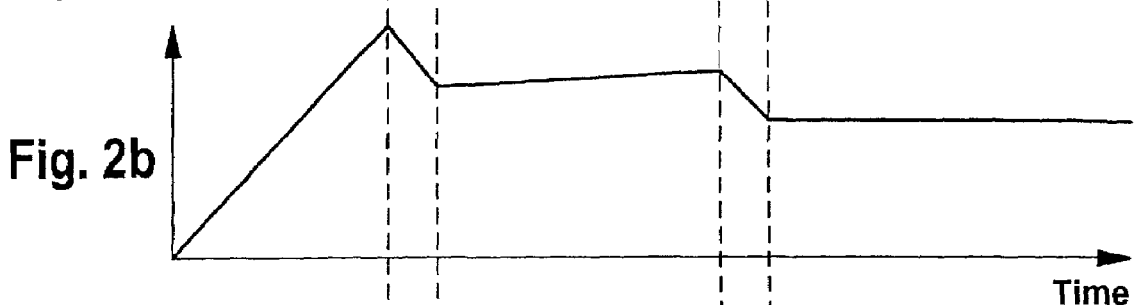
FIG. 2b is a graph of the intraperitoneal volume vs. time during dialysis treatment.
Figure 2C:
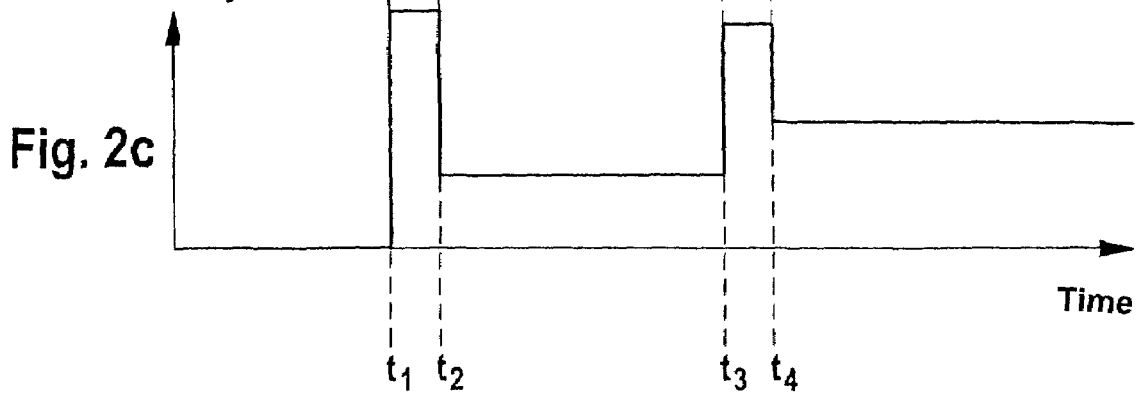
FIG. 2c is a graph of the ultrafiltration rate vs. time during dialysis treatment.

The control unit 22 now provides the following sequence of measurements. First the control unit 22 provides an ultrafiltration rate of 0, i.e., the ultrafiltration pump 18 is at standstill (FIG. 2c). Now the albumin concentration in the peritoneal solution slowly increases (FIG. 2a). At the same time the intraperitoneal volume also increases (FIG. 2b). At time $t_1$ the measuring unit 10 measures the albumin concentration co in the peritoneal solution. Subsequesntly, the ultrafiltration rate is briefly increased, in order to withdraw a predetermined quantity of fluid from the first circuit 19 (FIG. 2c). Tests have shown that withdrawal of a quantity of fluid of 200 to 800 mL is adequate for sufficiently accurate determination of the intraperitoneal volume. At time $t_2$ the measuring unit 10 measures the albumin concentration $c_1$ again.

The calculating and evaluation unit 24 calculates the intraperitoneal volume (V) from the withdrawn volume ($\Delta V$) and the albumin concentration ($c_0$ and $c_1$) according to the following equation:

$$V = \frac{\Delta V}{1 - c_0/c_1}$$

At the same time, the calculating and evaluation unit 24 calculates the patient's ultrafiltration rate V (t₁)/t₁ from the albumin concentrations $c_0$, $c_1$. In the further course of treatment the control unit 22 then provides an ultrafiltration rate that corresponds to the patient's ultrafiltration rate. At a later time $t_3$ measurement of the intraperitoneal volume is repeated according to the procedure described above and the ultrafiltration rate of the machine is adjusted to the possibly altered ultrafiltration rate of the patient. It is crucial that the increase in albumin concentration between the two times $t_1$, $t_2$ and $t_3$, $t_4$ be disregarded, so that secretion and resorption of albumin have no influence on the result of measurement.

Should the concentration of the endogenous substance to be measured not be negligible during the measurement period, the result of measurement may be corrected, for example, linearly by measurements of concentration at additional times $t_1$, $t_2$.

Instead of a withdrawal of fluid, a controlled addition of fluid into the patient's circuit is alternatively possible. This may be done by, for example, suitable control of the balancer 12 by the control unit 22. The fluid is then pumped into the patient's circuit via the dialyzer 8. Direct delivery of fluid into the patient's circuit via a pump (not represented) is alternatively possible. In this way determination of the intraperitoneal volume may alternatively take place by dilution instead of by concentration of an endogenous substance.

Figure 3:
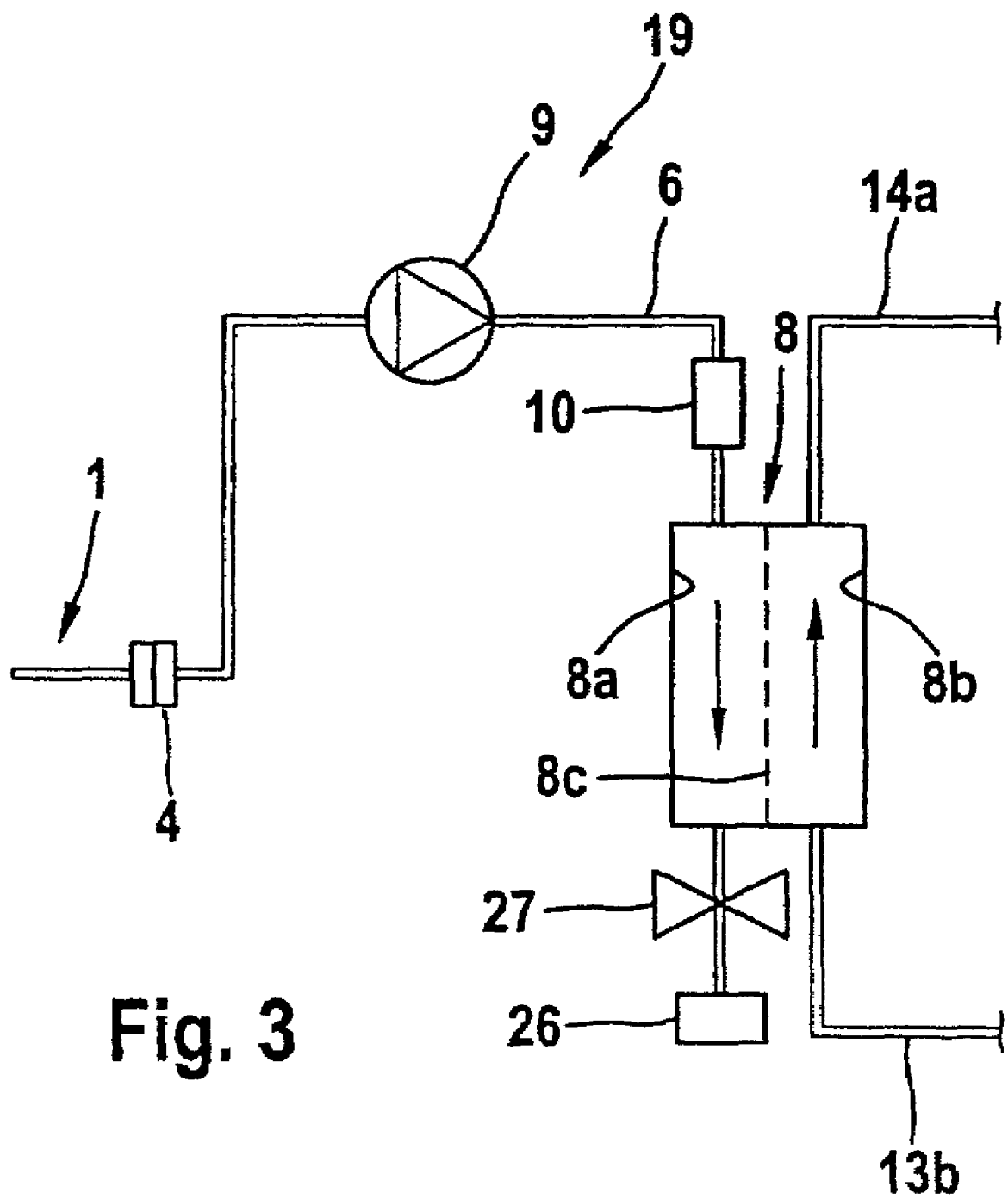
FIG. 3 illustrates, a second example of a peritoneal dialysis device having a means for determining the peritoneal volume.

FIG. 3 shows a second example of the peritoneal dialysis device. Only the parts of the device by which the device of FIG. 3 differs from the device of FIG. 1 are shown. Otherwise, the design of the two devices is the same. Like reference numerals are used for like parts. The means for determining the intraperitoneal volume of FIG. 3 corresponds to that of FIG. 1.

The peritoneal dialysis device of FIG. 3 has no drain line for returning peritoneal solution from the first compartment 8a of the dialyzer to the patient's peritoneal cavity. The outlet of the first compartment 8a of the dialyzer 8 is closed by means of a hydrophobic filter 26 that is permeable to air but impermeable to fluid. In addition, a valve 27 is arranged before the hydrophobic filter. The pump 9 first pumps peritoneal solution from the patient's peritoneal cavity by way of a single-lumen catheter into the first compartment 8a of the dialyzer 8, the valve 27 being closed. Then, the direction of rotation of the pump 9 is reversed and the valve 27 opens, so that the pump 9 pumps the peritoneal solution from the first compartment 8a of the dialyzer 8 back into the peritoneal cavity again. In so doing, the first compartment 8a of the dialyzer 8 is ventilated by way of the hydrophobic membrane 26.

Determination of the intraperitoneal volume takes place by a concentration measurement similar to that of the device described with reference to FIG. 1.

While the foregoing description and drawings represent the preferred embodiments of the present invention, it will be apparent to whose skilled in the art that various changes and modifications may be made therein without departing from the true spirit and scope of the present invention.

What is claimed is:

1. A method for determining an intraperitoneal volume during peritoneal dialysis, comprising the steps of:
    passing a peritoneal solution from a peritoneal cavity in a first circuit adjacent a first side of a semipermeable membrane; passing a dialyzing fluid in a second circuit adjacent a second side of the semipermeable membrane;
    measuring the concentration of an endogenous substance in the peritoneal solution, wherein the endogenous substance passes through a peritoneum into the peritoneal solution in the peritoneal cavity; and
    determining the intraperitoneal volume from the variation in the concentration over time.

2. The method according to claim 1, wherein the measuring step further comprises:
    measuring the concentration $c_0$ of the endogenous substance in the peritoneal solution at a time $t_1$;
    withdrawing or delivering a predetermined volume $\Delta V$ of fluid in the first circuit;
    measuring the concentration $c_1$ of the endogenous substance in the peritoneal solution at a time $t_2$; and
    wherein the determining step further comprises:
    determining the intraperitoneal volume from the equation:

$$V = \frac{\Delta V}{1 - c_0/c_1}.$$

3. The method according to claim 2, which further comprises the step of:
    determining an ultrafiltration rate V (t₁)/t₁ from the variation in intraperitoneal volume in the time $t_1$-$t_2$;
    withdrawing fluid from the first circuit at the ultrafiltration rate.

4. The method according to claim 3, which further comprises the step of:
    determining continuously the variation in intraperitoneal volume during peritoneal dialysis for determination of the ultrafiltration rate.

5. The method according to claim 1, wherein the endogenous substance is albumin.

* * * * *